United States Patent [19]
Wohlgemuth

[11] Patent Number: 5,507,642
[45] Date of Patent: Apr. 16, 1996

[54] DENTAL TURBINE DRIVE

[75] Inventor: Juergen Wohlgemuth, Darmstadt, Germany

[73] Assignee: Siemens Aktiengesellscahft, Munich, Germany

[21] Appl. No.: 260,311

[22] Filed: Jun. 15, 1994

[30] Foreign Application Priority Data

Jun. 21, 1993 [DE] Germany .................. 43 20 532.1
Mar. 16, 1994 [EP] European Pat. Off. .......... 94104118

[51] Int. Cl.⁶ ..................................... A61C 1/05
[52] U.S. Cl. ............................... 433/132; 415/904
[58] Field of Search ..................... 433/132, 91, 114, 433/115; 415/904

[56] References Cited

U.S. PATENT DOCUMENTS

| | | | |
|---|---|---|---|
| 3,306,375 | 2/1967 | Macks | 433/132 |
| 3,542,372 | 11/1970 | Edwardson | 433/116 |
| 3,762,052 | 10/1973 | Melde . | |
| 4,435,161 | 3/1984 | Masimann | 433/132 |
| 5,158,456 | 10/1992 | Lilley | 433/116 |
| 5,340,312 | 8/1994 | Murase | 433/132 |

FOREIGN PATENT DOCUMENTS

| | | |
|---|---|---|
| 0497139 | 8/1992 | European Pat. Off. . |
| 6098899 | 4/1994 | Japan .................. 433/114 |
| 632405 | 10/1982 | Switzerland . |

*Primary Examiner*—Cary E. O'Connor
*Attorney, Agent, or Firm*—Hill, Steadman & Simpson

[57] ABSTRACT

A dental turbine drive which is provided with an arrangement to prevent suctioning of particles after deactivation of the drive air into the return air line. To accomplish this, the turbine space is closed during a run-out phase of the rotor except for an outflow channel that is arranged close to the axis of the rotor shaft adjacent the tool side and is connected to a return air channel. The return air channel can discharge directly into the outflow channel at a point spaced from the main portion of the rotor and a valve arrangement may be presented for closing the air opening once the input air has been interrupted.

13 Claims, 2 Drawing Sheets

DENTAL TURBINE DRIVE

BACKGROUND OF THE INVENTION

The present invention is directed to a dental turbine drive having a housing with a rotor or turbine space and a rotor having shafts extending from each side being mounted for rotation by bearings in the turbine space with one end of one shaft portion extending from the housing and having means for accepting a processing tool, the housing having an air drive channel for supplying and directing air onto the rotor and a return air channel for removing air from the turbine space.

A problem in present dental turbine drives is that the air and, thus, bacterially contaminated particles can be suctioned in from the immediate environment, such as the oral cavity of the patient after the drive air has been shut off. This is due to the continued rotation of the rotor or turbine in a run-down or run-out phase creating eddy currents or a suction which will be conveyed into the inside of the turbine handpiece. When the drive air is subsequently reactivated, these particles are then again conveyed outward from the handpiece by the pressure being built up within the drive air supply.

This event is extremely unhygienic and harbors the risk of transmitting morbific agents. In addition, the rotor bearings can be damaged due to the penetration of, in particular, humid air and/or superfine particles.

The suction effect is caused by the rotor that, after the drive air is shut off, requires several seconds due to its mass moment of inertia and due to the high speed to run down or come to a standstill. During this run-down phase, the decelerating rotor in the turbine housing acts like an impeller pump and radially centrifuges the air located in the rotor chamber or space radially outward into the return air channel that is arranged in the outer circumference of the rotor chamber in most known turbine handpieces. The underpressure or suction will occur in the region of the rotor shaft, and this will result in the flow of the air from the outside through the existing bearing gaps or other openings.

A number of proposed solutions have been disclosed in order to prevent the above-mentioned aspiration effect. DE 11 47 003 and 11 07 891 both disclose that compressed air can be blown into the rotor chambers after the shut-off of the drive air feed until the rotor comes to a standstill. This method is extremely effective in and of itself, but is dependent on the supply of the dental apparatus to which the turbine drive is connected. Moreover, the technical outlay and cost for controlling the after-blowing is substantial.

EP-0 283 417 discloses a turbine drive wherein a mechanical brake acting on the rotor is intended to effect a rapid stopping of the rotor after deactivation of the drive air. Although such means for creating a rapid stop for the rotor is fundamentally desirable, it can be achieved only with relatively great technical outlay given the known turbine drive.

EP-0 471 961 discloses a turbine drive wherein a spin disc is put in place on the rotor shaft, only preceding the tool-proximate bearing, and this spin disc is intended to prevent the penetration of particles in that these are hurled radially outward when they impinge on the disc. Such an arrangement is, in fact, extremely simple but does not satisfactorily prevent the penetration of particles, since the suction effect at the rotor side is not eliminated.

SUMMARY OF THE INVENTION

The present invention is directed to an object of creating a dental turbine drive wherein an effective prevention of back-absorption of particles is established, namely with minimum technical outlay. The means to be provided, moreover, should function independently of the air supply to the turbine.

To accomplish these goals, the present invention is directed to an improvement in a dental turbine drive having a housing with a turbine space, a rotor having a first shaft portion engaged with a first bearing and a second shaft portion engaged with a second bearing, said rotor being mounted by said bearings for rotation in the housing with the first shaft portion extending from the housing and having means for holding a processing tool, said housing having a delivery channel for directing a flow of air on the rotor and a return air channel for removing air from said housing. The improvements comprise means for preventing a suction of air through the bearings adjacent the shaft portion into the return air channel during a run-down phase of the rotor, said means including providing a large air gap along one face of the rotor adjacent the one shaft portion, and positioning the air return channel adjacent this enlarged air gap, providing valve means for closing the return air gap once the pressure in the delivery channel drops.

In another embodiment, the means includes providing an air flow channel extending along the axis of the first shaft portion with a diameter of the outflow channel being substantially less than the diameter of the turbine space and with the return air channel being connected to the outflow channel adjacent the first bearing. Thus, the return air channel is spaced a greater distance from the rotating blades. It is also possible to provide air guide vanes on the first shaft portion which are constructed to direct air flow generally in a direction along the shaft away from the rotor toward the tool received in the means for holding the tool. Combinations of the above modifications and embodiments can be utilized to accomplish the same effect.

Other advantages and features of the invention will be readily apparent from the following description of the preferred embodiments, the drawings and claims.

DESCRIPTION OF THE PREFERRED EMBODIMENTS

Figure 1:
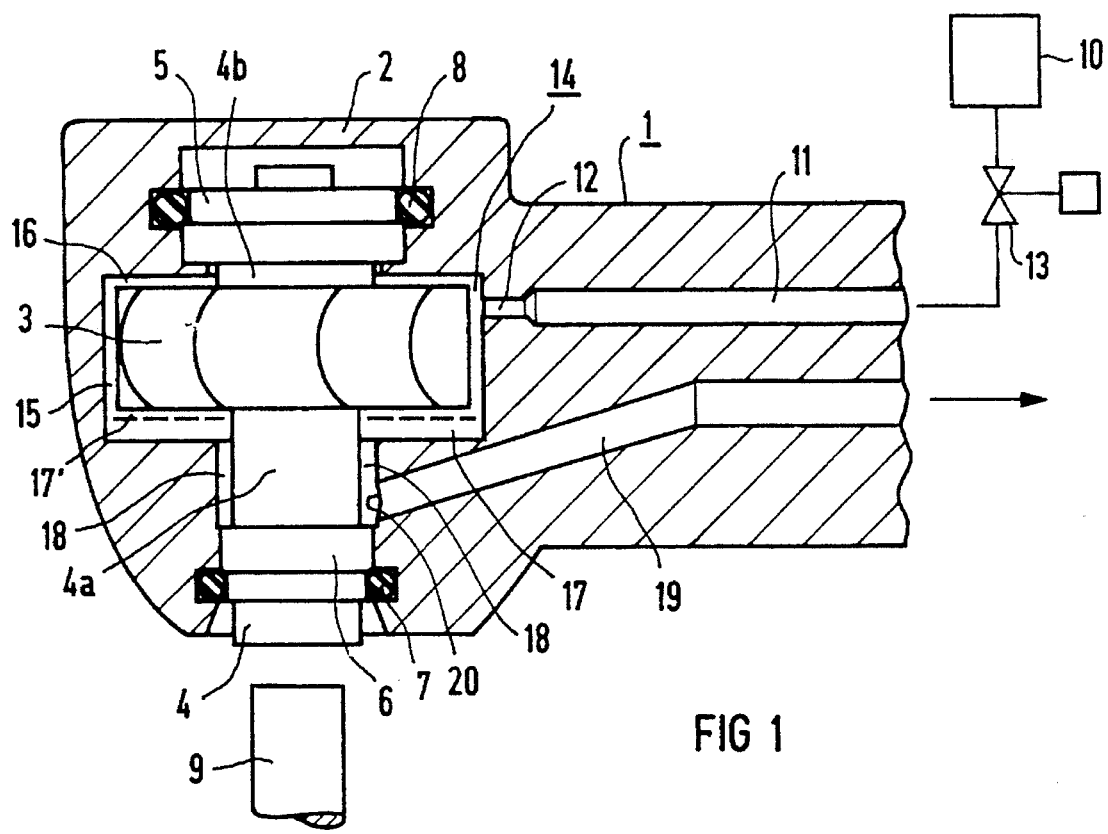
FIG. 1 is a cross sectional view of a head housing of a dental handpiece containing a dental turbine having the improvements in accordance with the present invention.

The principles of the present invention are particularly useful when incorporated in a head housing 2 of a dental turbine handpiece, generally indicated at 1 in FIG. 1. The head housing 2 has a turbine space 14 which receives a rotor 3 a shaft 4 with shaft portions 4a and 4b. The rotor 3 is mounted in a space 14 with the shaft portion 4a being mounted by a first bearing 6 and the second shaft portion 4b being mounted by a second bearing 5. The bearings 5 and 6 can be ball bearings and they are supported in the housing by O-rings 7 and 8. In a known way, the first shaft portion 4a extends out of the housing and contains means, such as a chuck or socket, for holding a processing tool 9, for example a drill. The rotor 3 is supplied with drive air from a compressed air source 10 via a delivery channel 11, which terminates in a nozzle 12 for directing the air flow onto the turbine blades. The drive air can be connected and disconnected by a valve 13.

Figure 2:
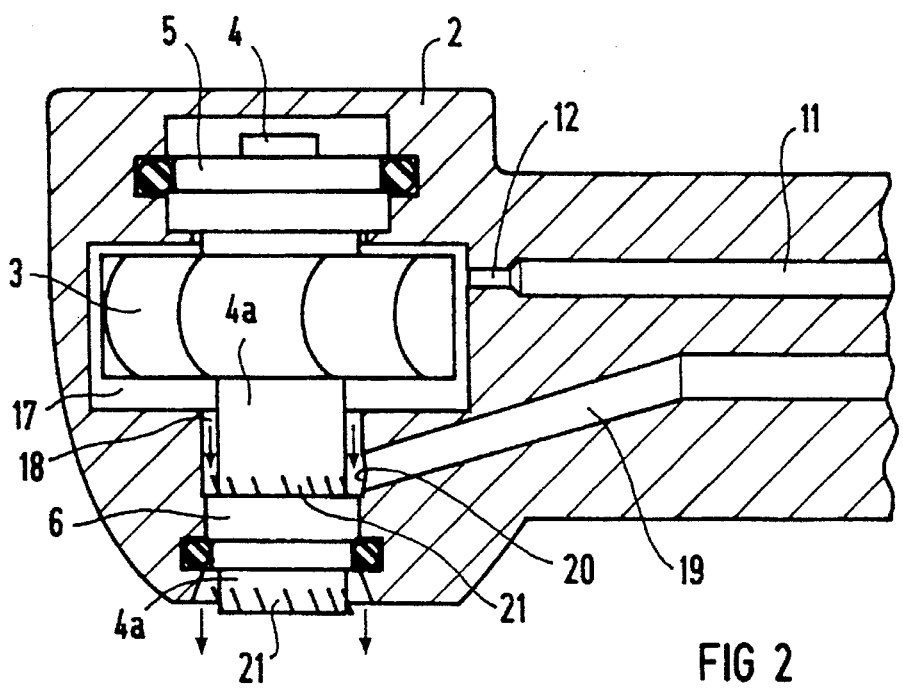
FIG. 2 is a cross sectional view of a dental handpiece having a modification of the invention of FIG. 1.

The flow path of the drive air in the turbine space 14 between the inlet into the space and the outlet from the rotor is normally limited by narrow air gaps that are formed between the rotor and neighboring housing and bearing walls. In the Figures, these are referenced as 15, 16 and 17'. The narrow air gap 17', which is indicated in the Figure by an interrupted or broken line, is usually present in the prior art at the end face of the rotor facing the tool. In the present invention, this space is enlarged to form a space of an outflow chamber 17 that merges into an outflow channel 18 extending concentrically relative to the first rotor shaft section 4a. This outflow channel 18 in the embodiment of FIGS. 1 and 2 is preferably fashioned so that it is an annular channel. The return air line 19 discharges into this annular channel, namely immediately adjacent to the first ball bearing 6 of the tool side, and has a discharge opening 20 which is immediately adjacent the first ball bearing 6.

Other than the delivery nozzle 12 and the discharge opening 20 for the return air channel 19, the housing 2 surrounding the rotor has no further channels and openings that could enable a free emergence of air in the peripheral region of the rotor and of the bearings. When the drive air is shut off or, respectively, given an uninterrupted delivery of the drive air in the run-out phase of the rotor, this means that the turbine space 14 is closed except for the annular space 18 preceding proximate to the axis of the rotor shaft. The air centrifuged outward by the rotor during the run-down phase can, thus, not flow out and can, thus, also not draw any air via the rotor bearings.

As may be seen in the illustrated exemplary embodiment, the opening 20 via which the annular channel 18 is connected to the return air channel is located, first, in the shaft region of the rotor, wherein the diameter of the rotating system is smallest, and, second, in the immediate proximity of the bearing 6 of the tool side, which is as far as possible from the largest diameter of the rotating system. In such an arrangement, no significant wake or, respectively, suction effect can be formed, because the centrifugal forces on the air are extremely slight in the proximity of the discharge opening 20 due to the small shaft diameter and because the discharge opening and the bearing gaps of the bearing 6 are located in the same region and also correspond with the same rotor shaft section 4a. As a result thereof, no underpressure can be formed in the bearing gap relative to the return air or discharge opening 20.

A modification is shown in FIG. 2 and has the first shaft portion 4a, which faces toward the tool, being provided with guide vanes 21. These vanes 21 are arranged on both sides of the bearing 6 and are fashioned so that they will generate an air flow upon rotation of the rotor which is directed in the arrow direction from the inside toward the outside. Due to this air flow, a counter-ventilation is generated that, additionally, opposes the penetration of particles, aerosol, germs or the like through the bearing 6.

Thus, in this embodiment and its modification, the means for preventing suction is the positioning of the discharge opening 20 in a small diameter channel or extension of the turbine space at a position spaced from the rotor and adjacent the first bearing.

Figure 3:
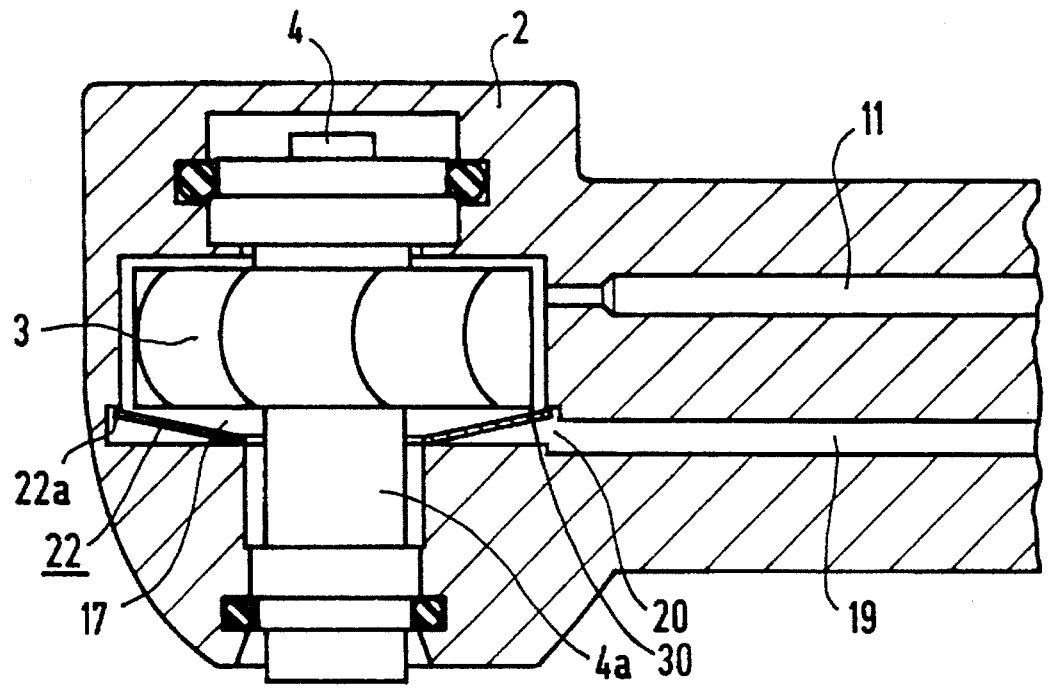
FIG. 3 is a cross sectional view of a head of a turbine handpiece having a second embodiment of the present invention, with the embodiment closing flow into the return air line.
Figure 4:
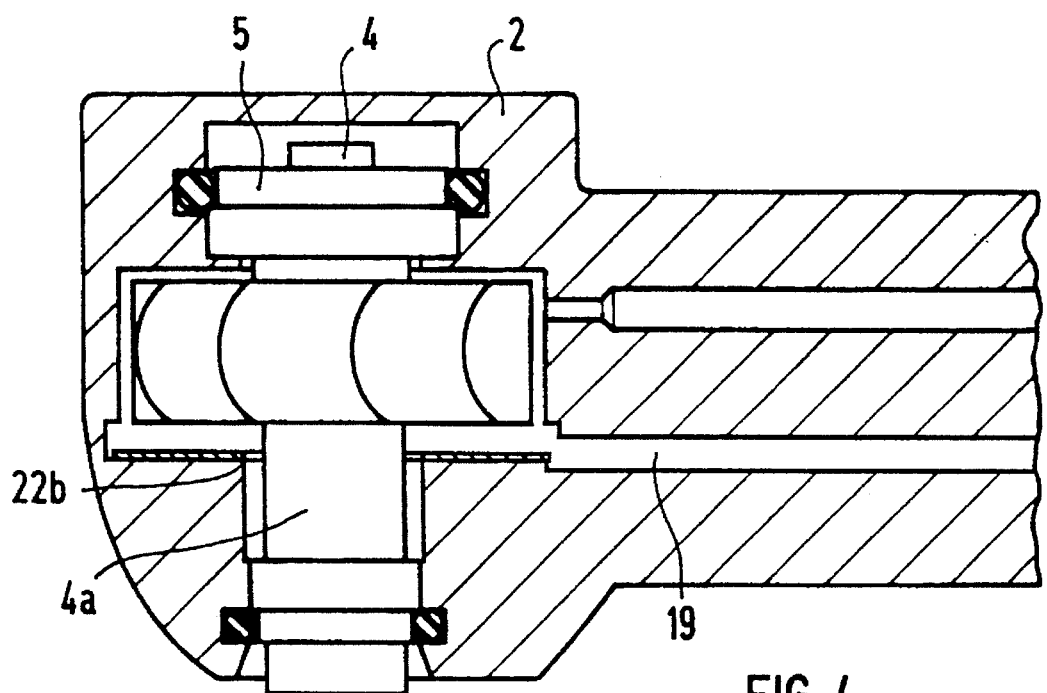
FIG. 4 is a cross sectional view of the dental handpiece of FIG. 3 with the valve arrangement open to allow the flow of return air.

A second embodiment is shown in FIGS. 3 and 4. In this second embodiment, a self-acting valve is provided concentrically relative to the rotor shaft 4, namely, likewise, neighboring the shaft section 4a on the tool side. This self-acting valve automatically closes the return air channel 19 or, respectively, return air opening when the drive air supply is interrupted or the drive air is shut off. The valve will open when the interruption in the air supply has been cancelled or removed and when the drive air is again turned on. One can, thus, effectively prevent drive air from being centrifuged into the return air channel during the rotor run-down phase and can effectively prevent air from being suctioned in via the bearings. The actuating power for this valve is directly produced by the drive air. In the exemplary embodiment shown here, the valve is composed of a resilient disc 22, for example a Belleville spring washer, that is arranged in the outflow channel 17 in the flow path between the rotor 3 and the return air channel 19. In this embodiment, the disc is mounted at the housing 2 concentrically relative to the rotor. When the drive air is shut off, for example when the rotor runs down and stands still, the disc 22 will close the return air channel with its outer annular wall surface 22a blocking flow into the discharge opening 20 (see FIG. 3). When the air drive is actuated, the disc is pressed downward against the spring power by the pressure being built up and, as a result thereof, the return air is again released, as shown in FIG. 4.

Various modifications are conceivable in view of the arrangement and fashioning of the resilient disc. Thus, it is conceivable to not mount the disc at the housing but at the rotor shaft. It is, likewise, conceivable to fix the disc with its outer annular wall surface and to realize the control of the return opening via the inner annular wall surface 22b. According to one advantageous fashioning, the disc can also be utilized as a rapid stop means for the rotor after the drive air is shut off. It is advantageous when the end face or edge 30 of the rotor facing toward the tool and the annular wall surface of the disc 22 corresponding to this end face contact one another for the purpose of a deceleration of the rotor when the drive air is shut off.

Thus, in the second embodiment of FIGS. 3 and 4, the means for preventing the flow includes a valve arrangement.

Although various minor modifications may be suggested by those versed in the art, it should be understood that I wish to embody within the scope of the patent granted hereon all such modifications as reasonably and properly come within the scope of my contribution to the art.

I claim:

1. In a turbine drive for a dental handpiece comprising a housing with a turbine space, a rotor having a first shaft portion with a first bearing and a second shaft portion with a second bearing being mounted by the bearings for rotation in the housing with the first shaft portion extending from the housing and having means for holding a processing tool, said housing having a delivery channel for directing a flow of air on the rotor and a return air channel with a discharge opening for removing air from the turbine space, said discharge opening being located between said bearings, the improvements comprising means for preventing suction of air through the first bearing and into the return air channel during a run-down phase of the rotor, said means for preventing including the turbine space being closed during the run-down phase of the rotor except for an outflow channel arranged close to the axis of the rotor shaft of the first rotor shaft portion and being connected to the discharge opening of the return air channel.

2. In a turbine drive according to claim 1, wherein the outflow channel extends from the turbine space along the first shaft portion, said discharge opening of the return air channel being adjacent the first bearing portion.

3. In a turbine drive according to claim 2, wherein the outflow channel is an annular channel that concentrically surrounds the rotor shaft on the tool side and has a diameter substantially less than the diameter of the rotor.

4. In a turbine drive according to claim 1, wherein the outflow channel is an annular channel that concentrically surrounds the rotor shaft on the tool side.

5. In a turbine drive according to claim 1, wherein said outflow channel is present on a face side of the rotor.

6. In a turbine drive for a dental handpiece comprising a housing with a turbine space, a rotor having a first shaft portion with a first bearing and a second shaft portion with a second bearing being mounted by the bearings for rotation in the housing with the first shaft portion extending from the housing and having means for holding a processing tool, said housing having a delivery channel for directing a flow of air on the rotor and a return air channel for removing air from the turbine space, the improvements comprising means for preventing suction of air through the first bearing and into the return air channel during a run-down phase of the rotor, said means for preventing including the turbine space being closed during the run-down phase of the rotor except for an outflow channel arranged close to the axis of the rotor shaft of the first rotor shaft portion and being connected to a discharge opening of the return air channel, and said means for preventing including said first shaft portion having guide vanes on a circumference in the tool proximate region, said guide vanes being constructed so that during rotation of the rotor, the guide vanes direct an air flow along the shaft portion toward the means for holding a tool.

7. In a turbine drive according to claim 6, wherein the guide vanes are arranged on said first shaft portions on both sides of the first bearing.

8. In a turbine drive for a dental handpiece comprising a housing with a turbine space, a rotor having a first shaft portion with a first bearing and a second shaft portion with a second bearing being mounted by the bearings for rotation in the housing with the first shaft portion extending from the housing and having means for holding a processing tool, said housing having a delivery channel for directing a flow of air on the rotor and a return air channel for removing air from the turbine space, the improvements comprising means for preventing suction of air through the first bearing and into the return air channel during a run-down phase of the rotor, said means for preventing including the turbine space being closed during the run-down phase of the rotor except for an outflow channel arranged close to the axis of the rotor shaft of the first rotor shaft portion and being connected to a discharge opening of the return air channel, and means for closing the discharge opening of the return air channel during the run-down phase of the rotor.

9. In a turbine drive according to claim 8, wherein the outflow channel is directly connected to the discharge opening of the return air channel and the means for closing the discharge opening of the return air channel closes the opening of the return air channel after interruption of the air drive supply and opens the discharge opening again after the interruption is eliminated.

10. In a turbine drive according to claim 9, wherein the closing and opening of the means for closing occurs automatically dependent on a compressed air supply.

11. In a turbine drive according to claim 9, wherein the means for closing includes a resilient means.

12. In a turbine drive according to claim 11, wherein the resilient means is a Belleville spring washer arranged in the outflow channel concentrically relative to the first turbine shaft portion, said Belleville spring washer having one annular edge surface selectively secured to one of the rotor shaft and housing and a second annular edge surface being positioned for closing the discharge opening.

13. In a turbine drive according to claim 11, wherein the Belleville spring washer is fashioned and arranged with the annular wall surface for closing the discharge opening being seated against a surface of the rotor for the purposes of decelerating the rotor when the drive air supply is interrupted.

* * * * *